(12) United States Patent
Ironside

(10) Patent No.: US 11,915,829 B2
(45) Date of Patent: Feb. 27, 2024

(54) PERIHEMATOMAL EDEMA ANALYSIS IN CT IMAGES

(71) Applicant: Natasha Ironside, Charlottesville, VA (US)

(72) Inventor: Natasha Ironside, Charlottesville, VA (US)

( * ) Notice: Subject to any disclaimer, the term of this patent is extended or adjusted under 35 U.S.C. 154(b) by 0 days.

(21) Appl. No.: 18/083,696

(22) Filed: Dec. 19, 2022

(65) Prior Publication Data
US 2023/0197275 A1 Jun. 22, 2023

Related U.S. Application Data

(63) Continuation-in-part of application No. 17/724,472, filed on Apr. 19, 2022.

(60) Provisional application No. 63/176,519, filed on Apr. 19, 2021.

(51) Int. Cl.
*G16H 50/20* (2018.01)
*G06T 7/00* (2017.01)
*G16H 20/10* (2018.01)
*G16H 20/40* (2018.01)
*G16H 30/20* (2018.01)

(52) U.S. Cl.
CPC .......... *G16H 50/20* (2018.01); *G06T 7/0014* (2013.01); *G16H 20/10* (2018.01); *G16H 20/40* (2018.01); *G16H 30/20* (2018.01); *G06T 2207/10081* (2013.01); *G06T 2207/20081* (2013.01); *G06T 2207/20084* (2013.01); *G06T 2207/30016* (2013.01)

(58) Field of Classification Search
CPC ........ G16H 50/20; G16H 20/10; G16H 20/40; G16H 30/20; G06T 7/0014; G06T 2207/10081; G06T 2207/20081; G06T 2207/20084; G06T 2207/30016
See application file for complete search history.

(56) References Cited

U.S. PATENT DOCUMENTS

| 7,676,257 B2 | 3/2010 | Suryanarayanan et al. |
| 9,165,360 B1 | 10/2015 | Bates et al. |
| 9,723,988 B2 | 8/2017 | Kakimoto et al. |

(Continued)

OTHER PUBLICATIONS

Natasha Ironside, MBChB; Ching-Jen Chen, MD; Dale Ding, MD; Stephan A. Mayer, MD; Edward Sander Connolly, Jr, MD, Perihematomal Edema After Spontaneous Intracerebral Hemorrhage, 2019, American Heart Association, pp. 1626-1633 (Year: 2019).*

(Continued)

*Primary Examiner* — Robert A Sorey
*Assistant Examiner* — Kimberly A. Sass
(74) *Attorney, Agent, or Firm* — Millen, White, Zelano & Branigan P.C.; William F. Nixon

(57) ABSTRACT

A system for perihematomal edema (PHE) analysis. The system includes a computing device receiving computerized tomography (CT) images from CT imaging devices. The CT images are associated with patients exhibiting perihematomal edema surrounding cerebral hematomas. CT images may be converted into feature vectors and passed as input to a convolution neural network model for identification and diagnosis of perihematomal edema volume changes. Detected changes may be thresholded to determine if the change represents an increase or shrinkage in the volumetry of the perihematomal edema.

19 Claims, 7 Drawing Sheets

|  | Fully Automated vs Manual | Fully Automated vs Semi-automated |
|---|---|---|
| Mean volumetric DC±SD | 0.838±0.294 | 0.843±0.293 |
| Mean Haussdorf distance, mm±SD | 202.09±252.51 | 259.22±306.45 |
| Mean surface distance, mm±SD | 5.69±14.97 | 6.50±13.88 |
| Mean relative volume difference, %±SD | 17.85±11.35 | 24.37±19.84 |

(56) References Cited

U.S. PATENT DOCUMENTS

| | | | |
|---|---|---|---|
| 10,282,663 B2 | 5/2019 | Socher et al. | |
| 10,347,010 B2 * | 7/2019 | Risman | G06V 10/774 |
| 2008/0292194 A1 * | 11/2008 | Schmidt | G06T 7/143 |
| | | | 382/131 |
| 2010/0260394 A1 | 10/2010 | Meetz et al. | |
| 2012/0114205 A1 | 5/2012 | Tang et al. | |
| 2012/0184840 A1 * | 7/2012 | Najarian | G06F 18/253 |
| | | | 600/407 |
| 2016/0210742 A1 | 7/2016 | Weiss | |
| 2016/0292864 A1 | 10/2016 | Dabbah et al. | |
| 2018/0365824 A1 | 12/2018 | Yuh et al. | |
| 2019/0019304 A1 | 1/2019 | Takei et al. | |
| 2021/0279880 A1 * | 9/2021 | Giner | G06T 7/0012 |

OTHER PUBLICATIONS

Natasha Ironside: "Fully Automated Segmentation Algorithm for Hematoma Volumetric Analysis in Spontaneous Intracerebral Hemorrhage" Stroke. 2019;50:3416-3423. DOI: 10.1161/STROKEAHA.119.026561.

Natasha Ironside:"Fully Automated Segmentation Algorithm for Perihematomal Edema Volumetry After Spontaneous Intracerebral Hemorrhage" Stroke. 2020;51:815-823. DOI: 10.1161/STROKEAHA.119.026764.

* cited by examiner

| | Fully Automated vs Manual | Fully Automated vs Semi-automated |
|---|---|---|
| Mean volumetric DC±SD | 0.838±0.294 | 0.843±0.293 |
| Mean Haussdorf distance, mm±SD | 202.09±252.51 | 259.22±306.45 |
| Mean surface distance, mm±SD | 5.69±14.97 | 6.50±13.88 |
| Mean relative volume difference, %±SD | 17.85±11.35 | 24.37±19.84 |

| Outcome | Manual | Semi-automated | Fully Automated | df | F Statistic | P Value |
|---|---|---|---|---|---|---|
| PHE volume, mean mL±SD* | 25.08±21.33 | 28.45±22.62 | 26.21±21.48 | 2,117 | 0.29 | 0.746 |
| Volumetric analysis time, mean seconds per scan±SD | 316.38±167.79 | 18.00±1.79 | 18.00±1.79 | 2,117 | 561.10 | <0.0001 |
| Pairwise Comparisons | Fully-Automated vs Manual | P Value† | Fully-Automated vs Semi-automated | P Value† | Semi-Automated vs Manual | P Value† |
| Difference in PHE volume, mean mL [95% CI] | 0.74 [-11.10, 12.59] | 0.988 | -2.04 [-13.89, 9.80] | 0.912 | 2.79 [-9.06, 14.63] | 0.842 |
| Difference in volumetric analysis time, mean seconds per scan [95% CI] | -298.38 [-402.48, -194.28] | <0.0001 | -462.50 [-566.60, -358.41] | <0.0001 | 164.13 [60.03, 268.22] | <0.0001 |

FIG. 7

PERIHEMATOMAL EDEMA ANALYSIS IN CT IMAGES

CROSS-REFERENCE TO RELATED APPLICATIONS

This application claims the benefit of priority under 35 U.S.C. 120 to provisional patent application No. 63/176,519 entitled "Fully Automated Segmentation Algorithm for Hematoma Volumetric Analysis for Spontaneous Intracerebral Hemorrhage" filed on Apr. 19, 2021 and provisional patent application No. 63/176,177 entitled "Fully Automated Segmentation Algorithm for Perihematomal Edema Volumetry after Spontaneous Intracerebral Hemorrhage" filed on Apr. 19, 2021. The contents of both applications are incorporated herein by reference in their entirety.

PERIHEMATOMAL EDEMA VOLUME ANALYSIS

The technical subject matter of this application relates generally to the field of patient condition diagnostics using medical image analysis. Specifically, the claimed subject matter relates to detecting changes in the volume of perihematomal edema.

BACKGROUND

Cerebral bleeding is a serious health problem affecting many people throughout their lifetime. Spontaneous cerebral bleeding occurs unpredictably or without warning. Various diseases can increase the risk of spontaneous cerebral hemorrhage including high blood pressure, blood clotting disorders and diabetes. Bleeding of the brain is particularly common in older individuals and in patients taking antiplatelet or blood thinning medications. Unlike surface or on-the-skin bleeding, internal bleeding within the cranial cavity can be difficult to detect and monitor. Medical imaging by specialized equipment is required in order to locate and visualize the bleeding; and further imaging is required in order to detect changes in hemorrhage patterns, including changes in the region surrounding the hemorrhage, termed perihematomal edema.

Current techniques for identifying brain bleeding use magnetic resonance imaging (MRI), computerized tomography (CT), or other types of scan technology to capture images of the cranial cavity. Physicians then review the captured images to determine whether there is evidence of a cerebral hemorrhage. Perihematomal edema occurs in the region surrounding the hemorrhage in a delayed fashion and represents injury to the surrounding brain tissue. By repeating medical images over time, physicians can detect changes in the volume of perihematomal edema surrounding the hemorrhage that could mean increased or reduced injury to the surrounding brain tissue caused by the effects of the hemorrhage including inflammation, and signs of changes to the underlying clinical state of the affected patient.

SUMMARY

Various embodiments are directed to a system for cerebral hematoma analysis. The analysis of CT images by an artificial intelligence model may increase the speed, efficiency and reliability of hematoma change identification. This in turn reduces diagnostic time and may improve patient outcomes.

One embodiment of the invention is a computing device including a processor, a display, a network communication interface, and a computer readable medium, coupled to the processor, the computer-readable medium comprising code, executable by the processor. The code may cause the processor to implement the steps of receiving, from a computerized tomography (CT) imaging device, a CT image of a patient exhibiting ICH and separating the CT image into CT image slices. The code may also include instructions for converting each CT image slice into a feature vector and passing the feature vectors to a convolutional neural network (CNN) model as input; then executing the CNN model to obtain an estimate of PHE volumetry. The estimate may be compared to a threshold, and based on the results of this comparison, determine a change in the medical status of the patient's PHE volume.

Additional embodiments include methods and processor-executable code stored on non-transitory computer-readable media for cerebral hematoma analysis. Systems for implementing these are also contemplated as embodiments.

Additional details regarding the specific implementation of these embodiments can be found in the Detailed Description and the Figures.

BRIEF DESCRIPTION OF THE DRAWINGS

FIG. 7 shows a table illustrating a comparison of performance parameters across CT image segmentation methods according to an embodiment.

DETAILED DESCRIPTION

Figure 1:
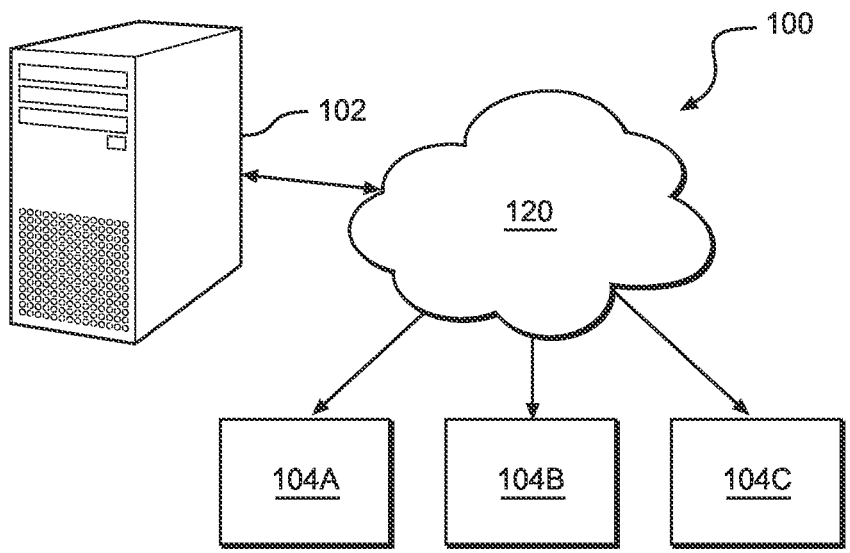
FIG. 1 shows a block diagram of a computing system environment suitable for implementing a PHE volumetric analysis system according to various embodiments.

Reference will now be made in detail to specific embodiments of the present invention. Examples of these embodiments are illustrated in the accompanying drawings. Numerous specific details are set forth in order to provide a thorough understanding of the present invention. While the embodiments will be described in conjunction with the drawings, it will be understood that the following description is not intended to limit the present invention to any one embodiment. On the contrary, the following description is intended to cover alternatives, modifications, and equivalents as may be included within the spirit and scope of the appended claims. Numerous specific details are set forth in order to provide a thorough understanding of the present invention.

Prior to discussing embodiments of the invention, some terms can be described in further detail.

A "computing device" may be a computing device that executes an application for artificial intelligence model building and use in diagnosing cerebral hematoma changes. A computing device may receive images from medical imaging devices with which it is in direct or networked communication. The computing device may maintain one or more data stores of image data, models, and software applications. This device may be a server, servers, workstations, personal computers (PC), tablets, and the like.

A "display" may be any electronic output device that displays or renders data in a pictorial or textual format. Displays may include computing device monitors, touchscreen displays, projectors, and the like.

A "CT imaging device" or "medical imaging device" may be a computerized tomography imaging device. The CT imaging device may be any device capable of using sensors to scan a portion of a patient's body and output CT image stacks of the sensor-collected data.

A "network communication interface" may be an electrical component that enables communication between two computing devices. A network communication interface may enable communications according to one or more standards such as 802.11, BlueTooth, GPRS, GSM, 3G, 4G, 5G, Ethernet, or the like. The network communications interface may perform signal modulation/demodulation. The network communications interface may include digital signal processing (DSP). Some embodiments may include computing devices that include multiple communications interfaces to enable communications according to different protocols or standards.

An "Electronic message" refers to an electronic message for self-contained digital communication that is designed to be transmitted between physical computing devices. Electronic messages may include but are not limited to transmission control protocol (TCP) messages, user datagram protocol (UDP) message, electronic mail, a text message, an instant message, transmit data, or a command or request to access an Internet site.

A "user" may include an individual or a computational device. In some embodiments, a user may be associated with one or more individual user accounts and/or mobile devices or personal computing devices. In some embodiments, the user may be an employee, contractor, or other person having authorized access to make use of a networked computing environment.

A "server computing device" is typically a powerful computer or cluster of computers. For example, the server computer can be a large mainframe, a minicomputer cluster, or a group of servers functioning as a unit. In one example, the server computer may be a database server and may be coupled to a Web server. The server computing device may also be referred to as a server computer or server.

A "processor" may include any suitable data computation device or devices. A processor may comprise one or more microprocessors working together to accomplish a desired function. The processor may include CPU or GPU comprising at least one high-speed data processor adequate to execute program components for executing user and/or system-generated requests. The CPU may be a microprocessor such as AMD's Athlon, Duron and/or Opteron; IBM and/or Motorola's PowerPC; IBM's and Sony's Cell processor; Intel's Celeron, Itanium, Pentium, Xeon, and/or XScale; and/or the like processor(s).

A "memory" may be any suitable computer-readable device or devices that can store electronic data. A suitable memory may comprise a non-transitory computer readable medium that stores instructions that can be executed by a processor to implement a desired method. Examples of memories may comprise one or more memory chips, disk drives, removable memory, etc. Such memories may operate using any suitable electrical, optical, and/or magnetic mode of operation.

Various methods and techniques described herein provide solutions for detecting changes in the size of perihematomal edema (i.e., inflammation and injury to regions surrounding the hemorrhage). Embodiments provide for the generation of one or more machine learning models that analyze computerized tomography (CT) scans of the cranial cavity of patients diagnosed with particular forms of cerebral hemorrhage. The output of the model(s) may provide estimates of the change in the volume, shape, and, or density of a patient's perihematomal edema across CT images. Diagnostic recommendations may be made based, at least in part, on the identified changes. These techniques may improve the speed, accuracy and precision of diagnosing changes in the brain region(s) surrounding the cerebral hemorrhage to enable health care providers to more quickly and appropriately administer care interventions.

Spontaneous intracerebral hemorrhage (ICH) affects approximately 15 to 25 per 100,000 persons worldwide. It is associated with high rates of mortality and functional disability. Patients who survive the initial impact of spontaneous ICH are at risk of delayed neurological injury. This is promoted by inflammatory and cytotoxic responses to the hematoma and its breakdown components. Secondary brain injury is a serious risk for ICH patients. Perihematomal edema (PHE) is a promising surrogate marker of secondary brain injury after ICH because it is a common endpoint for thrombin accumulation, inflammatory mediator influx, and erythrocyte lysis. Improvements in the accuracy, reliability, and efficiency of PHE quantification could permit administration of treatments for PHE to improve patient outcomes. Timely identification of the initial PHE volume and a change in that volume improves the likelihood that early intervention is performed on appropriate patients to positively affect patient outcomes.

Non-contrast CT is the most commonly used neuroimaging modality for PHE assessment in ICH patients, due to its pervasive availability and rapid image acquisition. Similarities in CT-based Hounsfield unit (HU) density between PHE, cerebrospinal fluid (CSF) and microangiopathy have limited the utility of threshold-based and edge-detection PHE segmentation diagnostic algorithms. The accuracy of semi-automated and manual PHE segmentation methods depends on the expertise of the rater; and these measurement techniques are both time-consuming and fraught with substantial measurement error. Accurate edge detection is important to the identification of changes in the volume of PHE.

The various embodiments provide solutions to the above-referenced challenges in edge-detection for identifying volume changes in PHE. The disclosed embodiments employ convolutional neural networks (CNN) in CT image analysis to overcome the limitations of currently available CT-based PHE identification and volume analysis. The various embodiments include computing devices, and systems, executing a method of generating and using a CNN model for fully automated PHE volumetry from CT scans of patients exhibiting cerebral hematomas.

For simplicity of illustration, a certain number of components are shown in FIG. 1. It is understood, however, that embodiments of the invention may include more than one of each component. In addition, some embodiments of the invention may include fewer than or greater than all of the components shown in FIG. 1.

I. The Analysis Environment

FIG. 1 illustrates an exemplary computing system 100 for PHE volumetric analysis according to various embodiments. With reference to FIG. 1, a system 100 may generate a CNN model based on the CT image scans of the cranial cavity of multiple patients. The CT images may be collected from patients via one or more CT imaging devices 104A, 1048, 104C and communicated or transmitted to a computing device 102 via a connection that is either direct or over a network 120. Image data may be stored in a data store accessible by the computing device 102. The collected CT images are used to train a CNN model to identify changes in the volume, shape, and/or density of PHE regions within patient images. The trained CNN model is then used by computing device 102 or other devices within the system 100 to diagnose PHE changes and recommend care interventions.

The system 100 includes one or more CT imaging devices 104A-C in communication with a computing device 102 capable of performing image segmentation, model training, model testing, and model use in diagnosing PHE region changes within CT images. Each of the CT imaging devices 104A-C is configured to perform CT imaging on a portion of a patient located within a scanning area such as within an enclosed region of the CT imaging device. The result of performing CT scanning of a portion of a patient is a CT image data file. The CT scan data is interpreted and converted to CT image data by CT imaging software applications local to the CT imaging device 104A-C or a control terminal connected thereto. Resulting CT image data includes multiple image slices, i.e. individual images. Either one or both of the CT scan data and CT image data may be stored locally for a temporary period of time or transmitted immediately to the computing device 102.

The system 100 may be a part of a broader research or healthcare computing environment and may connect any number of computing devices such as computing device 102 to various computing systems throughout the broader Organization via a network 120. The CT image analysis system 100 can include any suitable network infrastructure including servers, data stores (i.e., databases), computing devices, mobile communication devices, etc. Data generated by other computing systems of the Organization may be transferred and/or transmitted to the computing device 102 by one or more infrastructure components. As illustrated in FIG. 1, CT imaging devices 104A-C, which may be associated with different organizational units (e.g., different wings of a hospital), may transmit data related to CT imaging to the computing device 102 via the network 120.

The system 100 includes a networked environment in which the computing device 102 connects to the CT imaging devices 104A-C via a network 120. The network 120 enables the transmission of data such as CT image data to various computing devices throughout the networked environment. In some embodiments, the data may be stored in a network server or database (not shown) that is accessed via computing device 102. In other embodiments, the computing device 102 may be directly connected or in direct communication with the CT imaging device 104A. This may include the transmission of data from the CT imaging device 104A to the computing device 102 over a wired communications port and connected cable. The computing device 102 includes a combination of software, data storage, and processing hardware that enable it to receive, manipulate, and convert medical image data and use the image data to train and test a CNN model for diagnosing changes in perihematomal edema volumes. CT image data or an image stack derived therefrom is transmitted by imaging devices 104A-C over network 120 for collection and aggregation by computing device 102, which may organize and store the data in a data store. The CT image data may be aggregated until CT images from a threshold number of patients have been received from the CT imaging devices 104A-C and stored in the data store. A portion of the aggregated CT images are then used to train a CNN model to identify changes in the volumetry of PHE volumes illustrated in the CT images for a patient.

The data store may be any suitable data storage in operative communication with the computing device 102. For example, the data store may be stored in a memory of the computing device 102 or in one or more external databases. Location of the data store within system 100 is fungible, such that the data store may sit within any system of a broader healthcare or research Organization, so long as it is in communication with computing device 102. The data store may retain data generated, modified, or otherwise published by various systems of the Organization as part of CNN model generation, training, or subsequent CT image analysis completion. The data store may also store models, analysis scripts, or other frequently used software code used to perform analysis of the CT images obtained by CT imaging devices 104A-C.

The computing device 102 may employ multiple software modules including programming code instructing a processor of the computing device to analyze data CT image data received from the various CT imaging devices 104A-C. One or more CNN models may be generated and stored as part of a software application executing on the computing device 102, to enable quick and accurate analysis of image stacks derived from CT image data. Administrators may access the CNN model and perform CT image data analysis via a diagnostics application. Using the diagnostic application, administrators may create templates or scripts to expedite use of the CNN model for CT image data analysis. Executing data analysis using the templates or scripts may cause the processor of the computing device 102 to execute the CNN model in the same processing session without additional instructions from an administrator.

Personnel operating the CT imaging devices 104A-C complete CT imaging of patients to obtain CT scan data. During completion of a CT imaging session, physical and, or logical components of a CT imaging device 104A-C are accessed by personnel to take required action. For example, the action may include use of CT imaging sensors to generate CT scan data files, as well as the modification of files, generation of structured or unstructured data, and, or modification of structured or unstructured data. That is, the use of CT imaging sensors of the CT imaging devices 104A-C to scan portions of a patient body may result in the generation of various forms of CT scan data that is converted into CT image data. The CT image data may include image data, meta data, system data, and the like.

Software modules executing on the computing device 102 may separate aggregated CT image data and associated image stacks into test data and training data sets for use in generating a CNN model. The set of training data is used by a model training software module to train a CNN model to identify regions of a PHE region within an image, and the subsequent changes to the PHE region between CT images obtained during different CT imaging sessions. The set of training data is provided as input to the CNN model and the output is compared against manual measurements of PHE region changes. In this manner, the accuracy of the CNN model is checked before its deployment within the system 100 for live image analysis.

Applying the CNN model to CT image data results in the identification of a measurement of change in PHE volumetry between CT image sessions. Changes in PHE appearance (i.e., shape, size, density) between CT imaging sessions may indicate changes to the volume of the underlying PHE region, which may signify the secondary injury occurring as a result of the presence of the hematoma. CT image data from multiple CT imaging sessions may be used as input to the CNN model and the resultant measurements of difference stored in the data store. For example, an anonymized identifier of the patient maybe assigned during CT image capture, and all CT image analysis results may be stored in database fields associated with the patient identifier. Reports or summaries of CNN model results may be generated by the computing device 102 and transmitted to any requesting parties or stored in the data store for later use. In this manner, the results of the CNN model may be used to track changes over time of PHE volumes within a patient and enable caregivers to diagnose changes to a patient's medical condition.

Figure 2:
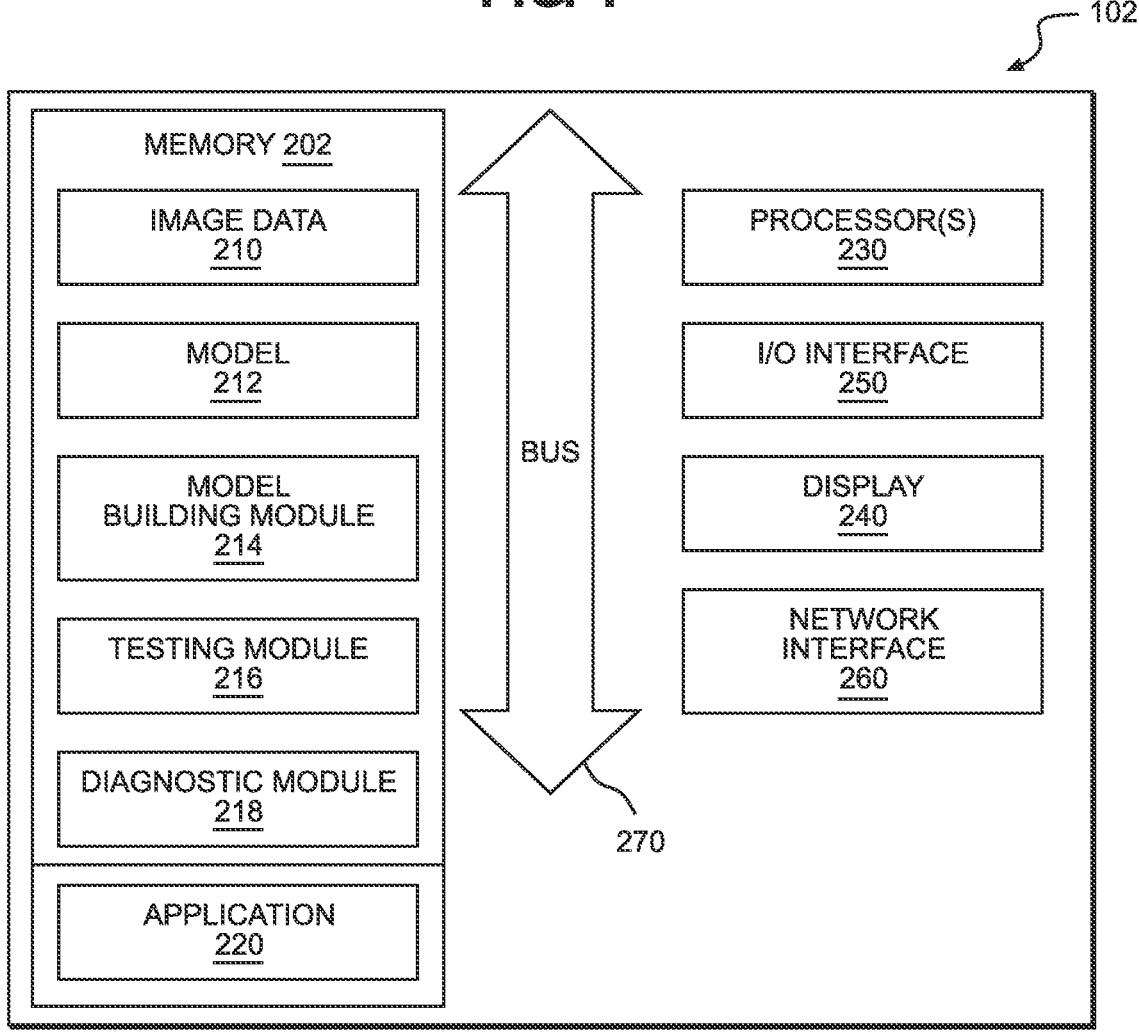
FIG. 2 shows a block diagram of a computing device according to various embodiments.

Referring now to FIG. 2, there is shown an example of a computing device 102 within which a set of instructions, for causing the computing system to perform any one or more of the methods discussed herein, may be executed. With reference to FIGS. 1-2, the computing device 102 may receive and analyze CT images from CT imaging devices 104A-C. In some implementations, the computing device 102 may create and execute a CNN model for analyzing CT images of PHE volumes, thus enabling the detection of changes to a patient's medical status with regard to the PHE volume.

In certain implementations, the computing device 102 may be connected (e.g., via a network, such as a Local Area Network (LAN), an intranet, an extranet, or the Internet) to other computer systems. The computing device 102 may operate in the capacity of server or a client computer in a client-server environment, or as a peer computer in a peer-to-peer or distributed network environment. Computing device 102 may be provided by a personal computer (PC), a tablet PC, a set-top box (STB), a Personal Digital Assistant (PDA), a cellular telephone, a web appliance, a network router, switch or bridge, or any device capable of executing a set of instructions (sequential or otherwise) that specify actions to be taken by that device. Further, the term "computer" shall include any collection of computers that individually or jointly execute a set (or multiple sets) of instructions to perform any one or more of the methods described herein for generating and executing a CNN model for identifying changes in PHE region via CT image analysis.

The computing device 102 includes a processing device such as a processor(s) 230, a memory 202 which includes a main memory (e.g., read-only memory (ROM), flash memory, dynamic random access memory (DRAM) (such as synchronous DRAM (SDRAM) or DRAM (RDRAM), etc.) and a static memory (e.g., flash memory; a static random access memory (SRAM), etc.), as well as a data storage device (e.g. data store), which communicate with each other via a bus 270.

Processor 230 represents one or more general-purpose processing devices such as a microprocessor, central processing unit, or the like. More particularly, the processing device may be complex instruction set computing (CISC) microprocessor, reduced instruction set computer (RISC) microprocessor, very long instruction word (VLIW) microprocessor, or processor implementing other instruction sets, or processors implementing a combination of instruction sets. Processor 230 may also be one or more special-purpose processing devices such as an application specific integrated circuit (ASIC), a field programmable gate array (FPGA), a digital signal processor (DSP), graphics processing unit (GPU), network processor, or the like. The processor 230 is configured to execute processing logic for performing the operations and steps discussed herein.

The computing device 102 may further include a network communication interface 260 communicably coupled to a network 110. The computing device 102 also may include a video display unit such as display 240 (e.g., a liquid crystal display (LCD) or a cathode ray tube (CRT)), an input/output interface 250 including an alphanumeric input device (e.g., a keyboard) and, or a cursor control device (e.g., a mouse), and an optional signal generation device (e.g., a speaker).

The memory 202 may include a computer-readable storage medium (e.g., a non-transitory computer-readable storage medium) on which may store instructions encoding any one or more of the methods or functions described herein, including instructions encoding applications 220 and modules 214, 216, and 218 for receiving CT image data, converting the CT image data into image stacks, sorting the data into testing and training sets, generating a CNN model to identify changes in PHE region from a CT image data input, and using the output of the CNN model CT image analysis to diagnose changes in PHE region and a patient's underlying medical status, which may also reside, completely or partially, within volatile memory and/or within processor(s) 230 during execution thereof by computing device 102, hence, volatile memory of memory 202 and processor(s) 230 may also constitute machine-readable storage media.

The non-transitory machine-readable storage medium may also be used to store instructions to implement applications 220 for supporting the receiving of CT image data, the building of a CNN model 212, and the use of that model to diagnose changes in PHE volumes within CT images of a patient. While the machine-accessible storage medium is shown in an example implementation to be a single medium included within memory 202, the term "machine-accessible storage medium" should be taken to include a single medium or multiple media (e.g., a centralized or distributed database, and/or associated caches and servers) that store the one or more sets of instructions. The term "machine-accessible storage medium" shall also be taken to include any medium that is capable of storing, encoding or carrying a set of instruction for execution by the machine and that cause the machine to perform any one or more of the methodologies of the disclosure. The term "machine-accessible storage medium" shall accordingly be taken to include, but not be limited to, solid-state memories, and optical and magnetic media.

One or more modules of processor-executable instructions may be stored in the memory 202 performing various routines and sub-routines of the methods described herein. For example, the model building module 214 may include instructions for executing the receiving of data from CT imaging devices 104AC, the formation of a training data set from the image data 210, and the use of that training data to build a CNN model 212 for analyzing CT images by the computing device 102. The testing module 216 may provide instructions for testing the CNN model 212 using a testing data set, which is a sample of the image data 210.

In various embodiments, the computing device 102 may also include diagnostic module 218 for diagnosing a change in medical status based on an identified change in the volume, shape, or density of a PHE region within a patient. For example, the output of the CNN model may be a measurement of difference in pixels, between two CT images including a PHE region of a patient. This measurement may be positive or negative indicating growth or reduction of volume, respectively. The measurement of difference may be compared to one or more thresholds to detect if the change is significant. That is, whether the change indicates a change in the patient's underlying medical status, such as expansion of a PHE region that indicates inflammation and injury to brain tissue surrounding the hematoma within the cranial cavity, or a reduction in volumetry which may indicate healing of the injury and absorption of the blood products.

The software applications 220 may provide additional functionality associated with the receipt and manipulation of CT data, as well as the storage and access of data within the data store. Applications 220 may enable the conversion of CT image data into DICOM images. The applications 220 may also assist in the addition, search, and manipulation of data-to-data store. That is, the applications 220 may provide support functionality for the model building module 214, the testing module 216, and the diagnostic module 218.

II. The Data Set

Various embodiments include the generation and testing of a CNN model using CT images in which a PHE region is presented surrounding and extending from or external to the border of the cerebral hematoma. In order to generate the CNN model, a data set of CT images of patients known to be experiencing PHE surrounding the spontaneous ICH must be curated. The data set consists of images of patients confirmed to have PHE surrounding the spontaneous ICH; the images having been reviewed and rated using one or more manual or semi-automated methods to segment and tag the PHE regions and thus differentiate PHE regions from the cerebral hematoma within the slices of CT images. Segmentation and tagging of the CT images in preparation for CNN model generation may including multiple phases to reduce noise and error.

Figure 3:
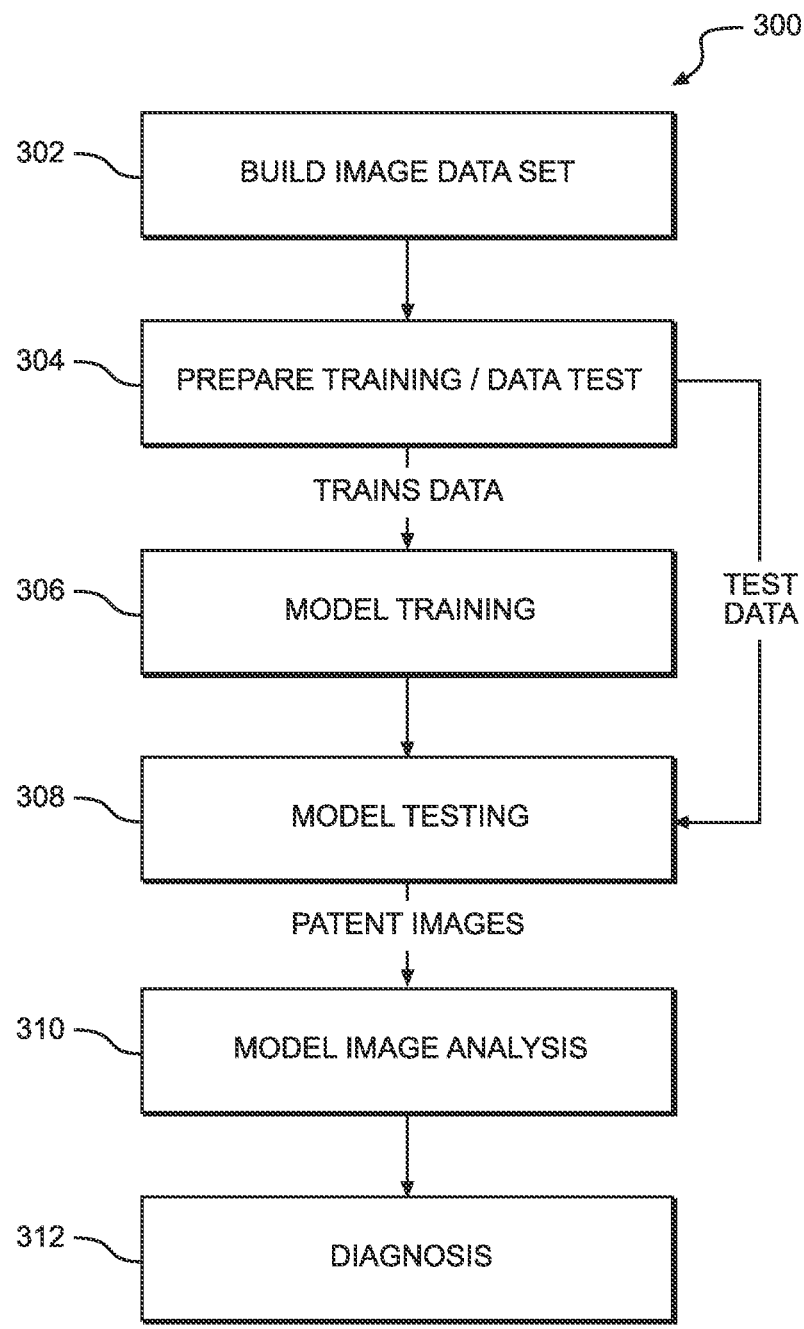
FIG. 3 shows a process flow diagram of generating a PHE volumetric analysis model according to various embodiments.

Referring now to FIG. 3, a method 300 for generating a CNN model for PHE volumetric analysis is shown. With reference to FIGS. 1-2, the computing device 102, may collect or aggregate a number of CT image scans of patient cranial cavity, i.e., brain images, and generate a CNN model using a portion of the collected CT images. The CNN model 212 is both trained and tested on tagged/segmented CT images to ensure accuracy. Once the CNN model output error is below an error threshold, it is deployed on incoming CT images as input to identify changes to a PHE region that suggests changes to a patient's medical condition.

By way of example, the model generation data set, e.g. N=400 patients may comprise a training data set, e.g. N=360 patients, including 464 in-patient CT images with a total of 14,953 2D image slices, all of which is stored in image data 210 within memory 202. The test data is the remaining portion of the model generation data set, e.g. N=40 patients, and comprises 40 in-patient CT images with 1,412 2D image slices. Baseline patient characteristics may be found to be comparable between the training and test cohorts.

Before training of the CNN model 212 can occur, CT images may be converted into Digital Imaging and Communications in Medicine (DICOM) image stacks having multiple 2D image slices. This may occur at the CT imaging devices 104A-C or at computing device 102. Thus, the conversion of CT image data into DICOM format may occur before or after transmission of the CT imaging data by the CT imaging devices 104A-C to the computing device 102. Thus, the image data 210 used to train the CNN model may be CT image data and/or DICOM image stacks.

The slices of each image stack must be reviewed and tagged, e.g. segmented, to provide the model with labelled data from which it can learn to identify the PHE region to compute its volumetry. As part of the segmentation process, CT images of ICH patients are evaluated for eligibility for their inclusion into a model generation data set. Images collected by the CT imaging devices 104A-C are reviewed by neurological imaging professionals and/or the processor 230 to ensure that the collected images meet inclusion criteria for addition into the model generation data set. Thus, the method 300 may begin with the collection, sorting, and segmentation of CT images received form the various CT imaging devices 104A-C. Neurological imaging professionals may review the images for presence and volume of a PHE region existing beyond the beyond the borders of the cerebral hematoma. In various embodiments, the volumetry of the cerebral hematoma may be tagged distinctively from the volumetry of the PHE region to enable the analysis process to detect changes in the degree of inflammation of the tissue surrounding the cerebral hematoma, which may indicate injury or damage to tissue not initially involved in the original ICH presentation. Proper segmenting of PHE regions is important for enabling the model to identify changes to previously healthy tissue that may require medical intervention that is supplemental to that given to address the original ICH.

In block 302, the model generation data set is composed and stored on the computing device 102. That is, the network communication interface 260 may receive CT image data and/or an image stack associated with CT image data via network 120 or directly from a CT imaging device 104A and the processor 230 may pass the received data to memory 202 for storage as image data 210. A portion of the stored image data 210 is selected for segmentation as part of generating the model generation data set. The model generation data set is made of a portion of the image data 210 and includes CT images of PHE surrounding supratentorial ICH locations from patients presenting spontaneous ICH. Some of the CT images obtained from the CT imaging devices 104A-C may be excluded from the model generation data set to reduce the presence of outlier image segments. The CT images excluded from the model generation data set may include those that show primary intraventricular hemorrhage, ICH with blood-fluid levels secondary to anticoagulant use that prevented quantification of the actual edema volume and ICH occurring secondary to trauma, brain tumor, hemorrhagic transformation of cerebral infarction, vascular abnormality or any other suspected secondary causes. Further, CT images obtained from CT scans performed (1) after surgical ICH evacuation or (2)>14 days after the ICH ictus may be excluded from the model generation data set. To ensure that exclusion criteria are correctly identified, CT image metadata may include location of ICH, ICH volume, the presence of associated IVH, and any suspected causes of the ICH. Exclusion criteria may be evaluated by the processor 230 by reviewing the metadata associated with CT image scans. In various embodiments, the metadata for received CT images is stored in the data store in association with the images and is part of the image data 210. Thus, the processor may check for exclusion criteria through a series of queries to the data store, without requiring a review of the actual image files to obtain metadata.

Selection of CT images for inclusion into the model generation data set is accomplished by selecting patient identifiers for a number of patients having CT scan images that do not meet the exclusion criteria. By way of example, CT images of 400 patients may be selected for inclusion in the model generation data set. The number of patients selected for inclusion into the model generation data set may be the same or less than the number of CT images selected for inclusion. This is because each patient may be associated with multiple CT images, and each CT image may have multiple slices. Various methods of selection may be used to identify patients for inclusion in the model generation data set. Patients may be selected in a manner that is consecutive, random, alternating, or the like.

In block 304, a user of the computing device 102 prepares the training and test data sets based on the collected CT images. For example, the processor 230 may execute applications 220 to enable segmentation of the CT images within the model generation data set and the separation of the resulting segmented images into testing data and training data sets. Proper image segmentation by human participants is an important part of CNN model generation. Accurate segmentation and identification of PHE regions within each slice of a CT image improves the accuracy of any CNN model trained using the segmented data. Thus, preparation of the data set is important to ensuring the efficacy of CNN model results in informing diagnostic decisions. Preparation of the collected CT images includes separation of the data set into a training set and a test set. Each slice of the CT images is then segmented manually by the user. A semi-automated technique may also be used in addition to the manual segmentation technique to compare segmentation results and reduce error.

To create the training set and the test set, identifiers for the patients whose images were included in the model generation data set may be shuffled in a random or pseudorandom manner and then divided into two groups. The first group, e.g., 40 patient identifiers of the randomly shuffled patient identifiers may be selected for the test group and the CT images corresponding to those patient identifiers are added to the test data set. The patient identifiers remaining in the randomly shuffled patient identifiers, e.g. 360 patient identifiers, are added to the training group and their corresponding CT images added to the training data set. Other techniques for separating the model generation data set into a test set and a training set may be used to generate the two data sets. Further, the number of patient identifiers included in each of the test set and the training set may vary.

In various embodiments, the process of segmenting the images of the training and test data sets may include two phases. The first phase includes the manual segmentation of CT image slices included in the training data set. Manual segmentation may be performed by a single user or a group of users arriving at a consensus. These manually tagged and segmented images may be used to generate and train the CNN model. The second phase of image segmentation includes the manual and, possibly, semi-automated segmentation of CT image slices within the test data set. The second phase of segmentation may be carried out by two or more users to ensure the accuracy of test set image segmentation. This second phase results are used to test and validate the trained CNN model's identification of PHE region changes.

In segmentation phase one, the CT images within the training set are manually segmented by one or more users. The PHE region hypodensity may be manually traced on each 2-dimensional (2D) slice of each 3-dimensional CT image stack using an input device connected to the input/output interface 250. A segmentation software application of applications 220 running on the computing device 102 may include processor-executable instructions to translate input device signals into annotations to the CT image slices. For example, the open-source software platform 3D Slicer 4.8 (National Institutes of Health, Bethesda, MD) or a similar CT image slice annotation software may be one of applications 220 and may be used for manual segmentation. Visual inspection and comparison to the contralateral hemisphere for identification of any hypodensity not otherwise attributable to PHE, by the one or more users, may be used to characterize the region of interest. The segmented training set is then used to train the CNN model.

In phase two of segmentation, a manual segmentation and possibly a semi-automated segmentation, are performed on the test data set. The semi-automated segmentation may be performed using a second segmentation software application of the applications 220, such as the Analyze 12.0 software platform (Mayo Clinic, Rochester, MN). For semi-automated segmentation, a temporary limit boundary is placed around the PHE region. After this, the input device is used to place a seed point within a region of interest of the PHE region. The region of interest may be identified manually by a user or estimated by the second segmentation software application. A region-growing Hounsfield Unit (HU) intensity threshold tool, set at 5-33 HU, may be utilized for PHE segment selection. The two or more users may manually adjust the HU threshold range to add or remove segments from the computer-selected region of interest at their discretion.

The test set is also manually segmented as described with reference to phase one. This provides a second reference set for the results of executing the CNN model on the test set. To improve reliability of user segmentations, repeat manual and, possibly, semi-automated segmentations may be performed in a subset of CT scans randomly selected from the test set after a minimal interval of time such as 7 days after the original segmentation rating.

The calculation of PHE region is mathematically similar for both manual and semi-automated segmentation methods. For both manual and semi-automated segmentation methods, measurements for each CT image slice are averaged across all of the phase two segmenting users to yield mean values. PHE region sizes are then calculated from CT images in the test set by multiplying the number of segmented voxels by the distance between each voxel in the x, y, and z dimensions The time required to complete PHE volumetry analysis for each CT is calculated and stored in the data store. In cases where more than one user performed segmentations on the same CT scan, the PHE region sizes, and the times required to complete PHE volumetry analysis, are averaged across all of the segmenting users to yield mean values.

$$\text{Area} = num_{vox} * x_{depth} * y_{depth} * z_{depth}$$

$$\text{Volume} = \frac{\text{Area}}{1000}$$

In various embodiments, the completion of segmentation phases one and two results in a set of reference images with segmented PHE regions for both the training data set and the test data set. In some embodiments, the segmented CT images may be stored in the data store as a reference training set and a reference test set. In other embodiments, only the segmentation geometry is stored for each CT image slice as a reference. That is, only the values of the segmentation size, border, and density may be stored in association with a CT image slice. In other embodiments, both the annotated CT image slices and the values of the segmentation size, density, and borders may be stored in association with the CT image slice in the data store. For each 3D PHE image stack, the segmentation values of the CT image slices of that stack may be used to calculate at least one overall volumetry value for the PHE volume presented within the CT image.

III. CNN Model Architecture

Figures 4, 5:
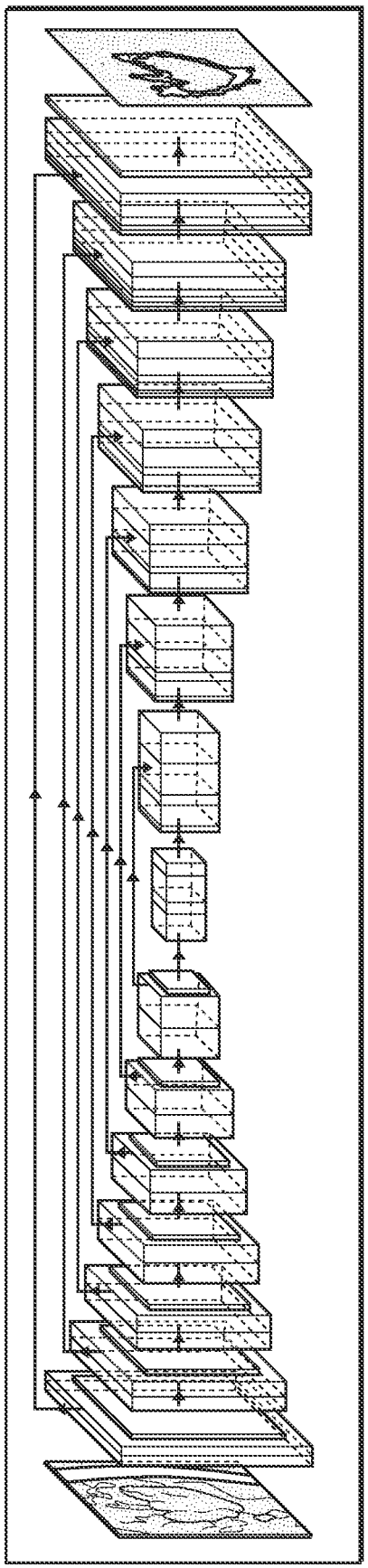
FIG. 4 shows a block diagram of a convolutional neural network for PHE volumetric analysis according to various embodiments.
FIG. 5 shows a data table illustrating performance parameters of a test data set according to various embodiments.
Figure 6A:
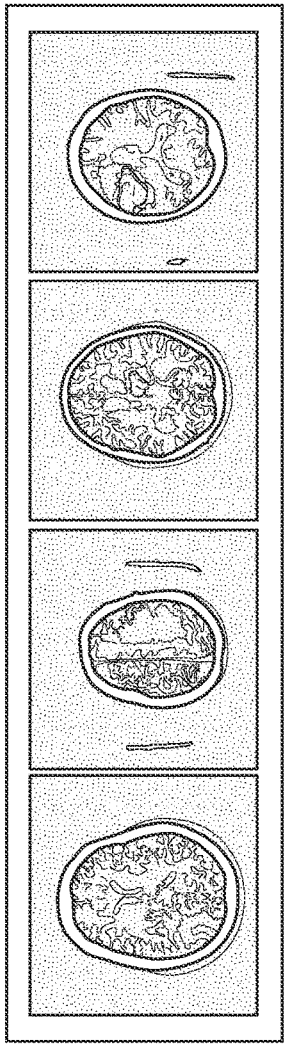
FIG. 6A shows CT image segmentations grouped by segmentation method according to various embodiments.
Figure 6B:
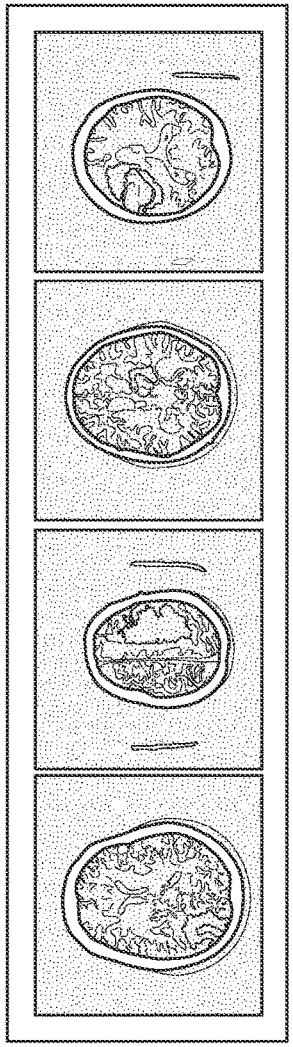
FIG. 6B shows CT image segmentations grouped by segmentation method according to various embodiments.
Figure 6C:
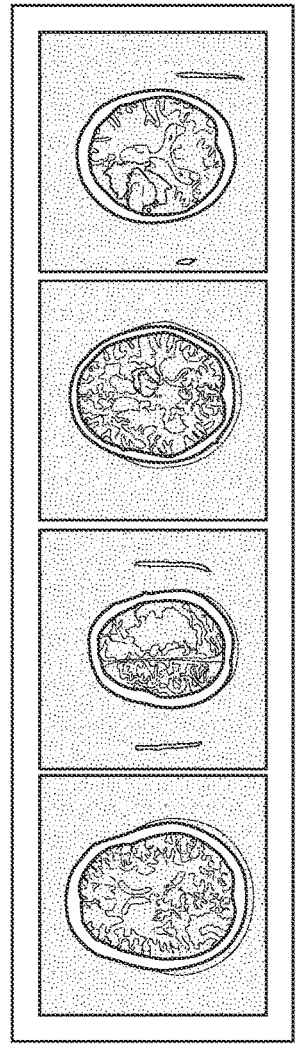
FIG. 6C shows CT image segmentations grouped by segmentation method according to various embodiments.
Figure 6D:
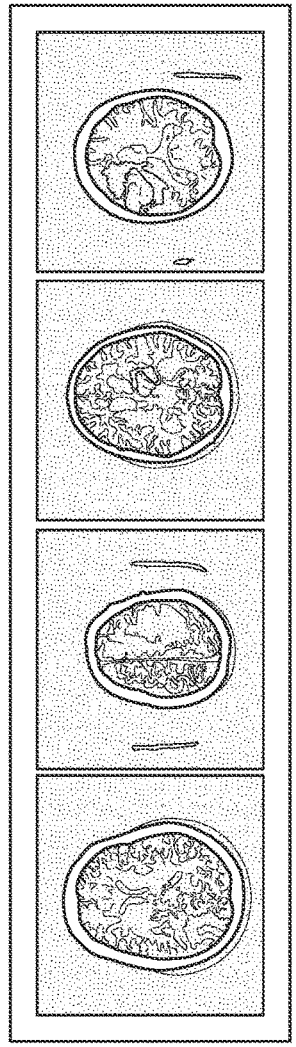
FIG. 6D shows CT image segmentations grouped by segmentation method according to various embodiments.

Referring now to FIG. 4, a CNN model architecture for PHE volumetry analysis according to the various embodiments is shown. With reference to FIGS. 1-3, the computing device 102 builds a CNN model 212 using the training data. The model 212 architecture may be well-suited to medical image processing and the identification of image regions within CT images. Selection of an architecture for the CNN model is important to ensuring that the CNN model 212 accurately identifies changes in PHE volumetry across CT images.

The CNN model 212 is designed to accept inputs of CT image data that has been pre-processed according to methods which may follow those detailed in subsequent sections. CT image stacks may be segregated into two-dimensional image slices for input into CNN model 212. Once the image slice has passed through the CNN model 212, the model may generate a two-dimensional binary segmentation of the PHE region. The corresponding CT image identifiers will be used to re-assemble three-dimensional image stacks. In some cases, the CNN model 212 may accept three-dimensional image stacks as the input and generate a three-dimensional segmentation of the PHE region volume. In embodiments in which the CNN model 212 accepts multiple CT image stacks that correspond to a single patient identifier, the resultant segmentation outputs are stored in the data store and changes in the segmentation size, border or density may be used to determine a change in the patient's medical condition.

To further the training data and testing data preparation, each 3D image stack and its corresponding manually segmented PHE region are converted into a feature vector. That is, features of the 2d slice and its manually segmented PHE region may be added to a 2-, 3- or 4-channel vector, e.g. a NumPy array. The feature vector may be resized to an input matrix of 1×256×256 using bicubic interpolation.

A threshold of 0 to 120 Hounsfield Units (HU) is applied to the original dynamic range. This removes the high-density bone of the skull, retaining the lower density structures that lie within the calvarium and the underlying ICH presentation. To further constrain the dynamic range, windowing may be performed by applying a HU range of, for example 0 to 70 HU, to the CT image and centering the image at a level of, for example 35 HU. The window of 0-70 HU enhances brightness and contrast to highlight the PHE from the surrounding brain issue structures and the volume, facilitating delineation of the PHE boundary or border. After conversion of the pixels of the 3D image stack of the CT scan and its manually segmented ICH region into a feature vector, the range of intensity values of the data representing the 3D image stack of the CT scan are organized to a normal distribution.

Normalization is performed by subtracting the mean and standard deviation of HU levels across all CT image stacks included in the model generation data set, for example, across 357 in-patient CT images. For each pixel of each 2D CT image slice, the mean is subtracted. The result is then divided by the standard deviation.

$\mu$=mean (images)

$\theta$=stdev (images)

$$\text{images}_{normal} = (\text{images} - \mu) \div \theta$$

Various types of noise may influence the image quality for image processing. These may include impulse noise which makes the intensity of a corrupted pixel much higher or lower than its neighbors, missing image samples which occurs when parts of the image are missing, damaged or partly occluded by undesired objects, damaged images which are caused by degradation due to lost or anomalous pixel values or packet loss which can occur during image transmission and/or tampering of the images. Restoration of the noisy images may be achieved by calculating the average values across all CT data which are then applied pixelwise to each slice. The normalized grayscale image channel vectors are contoured using a curvature driven image denoising algorithm. Incorporating the curvature of the image level preserves the edges of the image surface while simultaneously smoothing within the region of pixel noise. A morphological closing operation may also be performed on the manually segmented PHE region to correct noise.

In various embodiments, the CNN model 212 architecture is a contracting and expanding topology, similar to the U-Net convolutional network architecture for image segmentation. The CNN model 212 has a contracting path and an expansive path. The contracting path comprises repeated application of two padded convolutions of a fixed kernel size which defines the field of view of the convolution i.e. 3×3 pixels. The kernel size is selected to balance computational efficiency while preserving complexity of the image analysis technique. Padding adds zero value pixels to the borders of the feature vector to avoid cropping of the image after each convolution. Padding also standardizes the number of times that the convolution is applied to each grayscale pixel, irrespective of the pixel's location within the image. Each convolution is followed by a rectified linear unit (ReLU) and a 2×2 max pooling operation. The max pooling operation calculates the largest value of each field of view in the convolution. A 2×2 filter with a stride of 2 pixels for down sampling is used to simultaneously achieve a gradual reduction in the x and y dimensions of the feature vector, thereby avoiding large scale down sampling and inadvertent loss of relevant image characteristics. At each down sampling, the number of image channels is doubled. The number of image channels represents the depth of the image feature vector i.e. z dimension, whereby each channel responds to a different image characteristic. 3×3 padded convolutions, each followed by a rectified linear unit (ReLU) and a 2×2 max pooling operation with a stride of 2 for downsampling. Each step in the expansive path comprises an upsampling of the feature map a 2×2 convolution that halved the number of feature channels, a concatenation of the feature map (φ symbol), and two 3×3 convolutions, each followed by a ReLU. At the final layer of the CNN model 212, a 1×1 convolution is used to map each 64-component feature vector to the desired number of classes.

Each step in the expansive path comprises an up sampling of the feature vector using a 2×2 filter with a stride of 2 pixels. This is followed by a 2×2 convolution that halves the number of image channels. A concatenation is performed by stacking the feature vector from the expansive path with the corresponding feature vector from the contracting path, thereby linking the two feature vectors. The padded border of the feature vector from the contracting path is cropped as necessary to equalize the x and y dimensions between the two feature vectors. This step is followed by two padded convolutions of the fixed kernel size used for the contracting path, i.e. 3×3 pixels. Each convolution is followed by a ReLU. At the final layer, a convolution of a fixed 1×1 pixel kernel size flattens the three-dimensional feature vector with a depth of, for example, eight channels, into a two-dimensional feature vector with the desired number of classes. In this case, there are two classes, 0 and 1, whereby 1 represents PHE region and 0 represents no PHE region. In total, the CNN model may consist of, for example, 31 convolutional and 7 pooling layers. The number of layers is selected to balance computational efficiency with the complexity of the image analysis technique.

To help the CNN learn complex patterns in the data, non-linear properties are added. The ReLU activation function is used to add these non-linear properties by transforming the summed and weighted input of feature vectors to an output value which is fed into the next layer of the network. The ReLU outputs a small value for small or negative inputs, and a large value if its inputs exceed a threshold. This mimics the physiology of neurons which fire at a certain stimulus threshold.

Batch normalization may be used between each convolution and ReLU layer. The mean and the variance of the feature vector inputs are applied to organize the inputs by a normal distribution. This may reduce the effects of bias and outliers during the activation function, thereby improving efficiency and stability of the CNN.

Regularization methods may be employed, including dropout and L2 regularization. Dropout randomly selects pixels to be removed during training, giving greater weight to the adjacent pixels when making predictions. This reduces the sensitivity of the CNN to the importance of specific pixels and allows multiple independent representations to be learned by the CNN. This, in turn, results in a CNN that is capable of better generalization and is less likely to overfit the training data. Overfitting causes premature convergence to the training data, resulting in poor performance of the CNNs on the testing data, thereby resulting in inaccurate ICH border detection. 50% dropout may be used, which applies the highest possible variance to the normally distributed feature vector inputs. L2 regularization penalizes outlier pixels weighted with very high or very low values by making them close to zero.

The described architecture is particularly well-suited to the fine grain identification of regions of a CT image that indicate changes in PHE volumetry. This CNN model is trained and tested using the feature vectors derived from the segmented training data set and the segmented testing data set.

III. CNN Model Training and Testing

Development of a CNN model requires training the model with a tagged, training data set. The trained model is tested using a second tagged data set, to ascertain the accuracy of the CNN model's predictions. Training of a CNN model may require several rounds of training and refining weights of the model in order to improve accuracy of the CNN model predictions. Various embodiments include the use of the training data set and the test data set, which are used to train and test a CNN model for identifying changes in PHE volumetry within CT images.

In block 306 of method 300, the computing device may build a CNN model for PHE volumetry analysis in CT images. For example, the processor 230 may execute the model building module 214 to build and test a CNN model 212. Once trained, the CNN model 212 may be used to generate PHE segmentations from CT scans in the test data set. The performance of the CNN model 212 is primarily assessed using the volumetric DC (defined as the similarity between the tested and reference PHE segmentations for each CT scan, reported on a scale of 0 to 1, with 1 indicating identical segmented voxels between the tested and reference segmentations).

To improve spatial invariance, the feature vectors from the training data set may be augmented before they are used as model inputs. Introducing spatial invariance reduces bias and improves the ability of the model to adapt to various types of data acquired in a variety of conditions. For example, in a real-world setting, the model should be able to identify PHE regions in different orientations, without exposure to these specific orientations within the tagged training data set. This may be achieved by applying affine distortions, which include translation, rotation, scaling, and shear, to the feature vectors of the training data set. In living tissue, deformation is a common variation. An additional technique to improve spatial invariance is creation of elastic deformations. A deformation field is created using a matrix sized according to the dimensions of the feature vectors of the training data set. Each element of this matrix is randomly sampled from a Gaussian distribution with a mean of 0 and a standard deviation which represents the elasticity co-efficient. The elasticity co-efficient is set as a scale according to the dimensions of the feature vectors of the training data set, for example, such as 18 pixels. The maximum initial value for the random displacement is also set as a scale according to the dimensions of the feature vectors of the training data set, for example, such as 384 pixels. The displacement of each pixel is then converted to integer values and re-sized to the original feature vector dimensions using bicubic interpolation.

Before augmentation of the training data set, ⅕ of the data are segregated and retained in their original format as a reference set, while the remaining ⅘ of the data are transformed. The performance of the CNN model may subsequently be assessed on the previously segregated, unmodified data. Initial kernel weights were drawn from a Gaussian distribution. A pixel-wise Dice Co-efficient (DC) may be applied to the final feature map for loss function computation. The DC is defined as the similarity between the CNN output and the reference PHE segmentation corresponding to each CT scan input. This is reported on a scale of 0 to 1, with 1 indicating identical segmented volumetric pixels between the CNN output and the reference segmentation.

$$DC = \frac{2xy}{x+y}$$

Where x represents the number of segmented volumetric pixels in the CNN model output and y represents the number of segmented volumetric pixels in the corresponding reference from the training or test data set.

The loss function may be defined as the inverse of the DC.

Loss=1−*DC*

The loss function may be defined as the error function. Proceeding backwards through the network, the gradient of the error function is calculated, and this is termed backpropagation. The gradient of the error function is then used to update the weights of each kernel before the next forward pass through the CNN. These steps are termed optimization. Adam is an adaptive moment estimation optimizer which utilizes Nesterov momentum that may be used. The DC is another optimization method that adapts the learning rate for weight updates to both the mean and the variance of the gradient. This may be used to achieve a faster convergence towards the loss function minima. Network hyperparameters were tuned based on 5-fold cross-validation of the training dataset.

The CNN model 212 may be trained for numerous repetitions. For example, the CNN model 212 may be trained for 100 epochs using a batch size of 32 and an initial learning rate of 0.0001. The hyperparameters including the number of repetitions and initial learning rate may vary depending on the accuracy desired and the granularity of CT image resolution.

In block 308, the CNN model 212 is tested on CT images from the testing data set. For example, the processor(s) 230 may use the testing module 216 to test the accuracy of the CNN model 212. The trained CNN model 212 is used to generate PHE segmentations from CT images in the test data set and thereby identify changes in PHE region volumetry. The performance of the CNN model 212 is assessed using the volumetric DC, defined as the similarity between the tested and reference PHE segmentations for each CT scan.

Referring to FIG. 5, a data table 500 shows performance of the CNN model 212 using the test data set of the image data 210. Secondary performance parameters for the CNN model 212 include the Hausdorff distance. The Hausdorff distance measures the distance between two point sets. It can be used to assess for differences between the edges of two objects that may otherwise have adequate spatial overlap (spatial overlap is measured by the DC). The secondary parameters also include the mean surface distance, which is defined as the mean distance, in mm, between the edges of the tested and reference PHE segmentations for each CT scan in the training data set. Further, the secondary parameters include relative volume difference, which is defined by the equation below:

$$\text{Percent relative volume difference} = \frac{(x_{voxels} - y_{voxels})}{y_{voxels}} \times 100$$

Where x represents the number of segmented voxels (volumetric pixels) in the CNN output and y represents the number of segmented voxels in the reference from the test data set. The secondary parameters further include the mean and median segmented PHE volumes and the mean volumetric analysis time, which is defined as the sum of the number of seconds required to perform volumetric analyses for each scan divided by the total number of scans. Volumetric analysis is defined as the processes of performing PHE region segmentations and subsequent calculations of PHE region volumes from that segmentation.

The table in FIG. 5 compares the performance of the trained CNN model 212 performing fully automated segmentation on the CT images in the test data set to the reference images segmented using the manual segmentation method. The semi-automated segmentation may be performed using a second segmentation software application of the applications 220, such as the Analyze 12.0 software platform (Mayo Clinic, Rochester, MN).

With the manual segmentation method as the reference standard, the mean volumetric DC, Hausdorff distance, surface distance, and relative volume difference for the fully automated segmentation algorithm may be 0.843±0.293, 259.22±306.45, 6.50±13.88 mm, and 24.37±19.84%, respectively. FIG. 7 shows representative examples of the manual, semi-automated, and fully automated PHE segmentation methods.

Referring now to FIGS. 6A-D, there are shown exemplary CT images with PHE regions segmented according to various segmentation methods. With reference to FIGS. 1-6D, the CT images of the test data set may be segmented using manual, semi-automated, and fully automated PHE segmentations. Example results of PHE segmentation methods applies to CT images in the test data set are shown in different columns. Column A includes the original CT image slice to which segmentation methods are later applied. Column B includes the manual PHE segmentation results for the corresponding image in Column A. That is, the images appearing in column B are the result of applying manual segmentation methods to the CT image appearing in the same row of column A. Column C includes the results of applying semi-automated segmentation methods to the corresponding CT image in column A, in embodiments in which semi-automated segmentation is used. Column D includes the results of applying the fully automated segmentation (CNN model 212) to the corresponding CT image of column A. Thus, the CT images of FIG. 6 provide visual comparison of the results of the CNN model 212 to the reference segmented CT images of the test data set.

Referring now to FIGS. 7 and 8A-D, there are shown data tables comparing PHE volume and analysis across segmentation methods applied to CT images of the test data set. With reference to FIGS. 1-8D, the performance of the CNN model 212 may be analyzed by calculating and comparing various performance metrics. In the test data set, the mean segmented PHE volumes in the test data set are 25.08±21.33, 28.45±22.62, and 26.21±21.48 mL using the manual, semi-automated, and fully automated segmentation methods, respectively. Segmented PHE volumes may not be significantly different among the methods (P=0.746).

In the test dataset, mean volumetric analysis times are 316.38±167.79, 480.50±295.32, and 18.00±1.79 seconds/scan for manual, semi-automated, and fully automated PHE segmentation methods, respectively. The volumetric analysis times among the three segmentation methods may be different (P<0.0001). Fully automated PHE segmentation may be faster than both of the manual (mean difference −298.38 [−402.48 to −194.28] seconds/scan; P<0.0001) and semi-automated (mean difference −462.50 [−566.60 to −358.41] seconds/scan; <0.0001) segmentation methods as applied to CT images of the test data set. The semi-automated segmentation method was slower than the manual method (mean difference, 164.13 [60.03 −268.22] seconds/ scan; P<0.0001). The faster processing of PHE volumetry by the CNN model 212 therefore drastically reduces the amount of time needed to identify changes in PHE volumes in patients. The CNN model 212 is designed as an image analysis tool. Therefore, testing for similarity between segmented PHE images (i.e. DC, Hausdorff distance, mean surface distance and relative volume difference) estimates the CNN model 212 accuracy. However, the practical usefulness of CNN model 212 to detect PHE volume changes, is established by testing for similarity or lack of significant difference between PHE region volumes measured between manual clinician raters and the CNN model 212. When there is sufficient confidence in the CNN model 212 to identify changes in PHE region volumes without significant difference to the manual clinician raters but with significantly increased efficiency, the CNN model 212 may be deployed on real world CT image data of patients with ICH. This may lead to more rapid diagnosis of volume changes and enable speedier application of life-saving interventions.

Figure 8A:
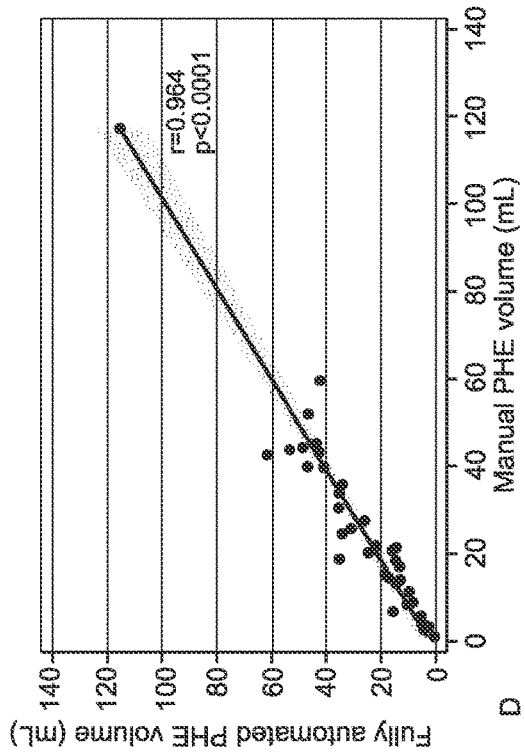
FIG. 8A shows scatter plot diagrams of PHE volume analysis across segmentation methods according to the various embodiments.
Figure 8B:
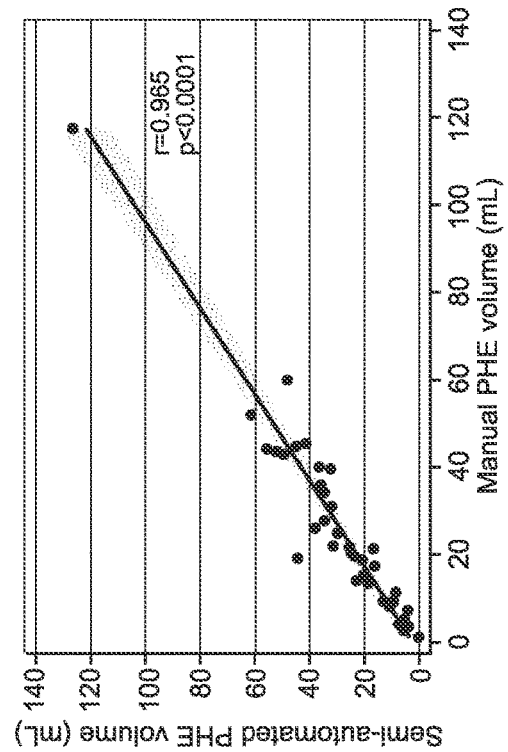
FIG. 8B also shows scatter plot diagrams of PHE volume analysis across segmentation methods according to the various embodiments.
Figure 8C:
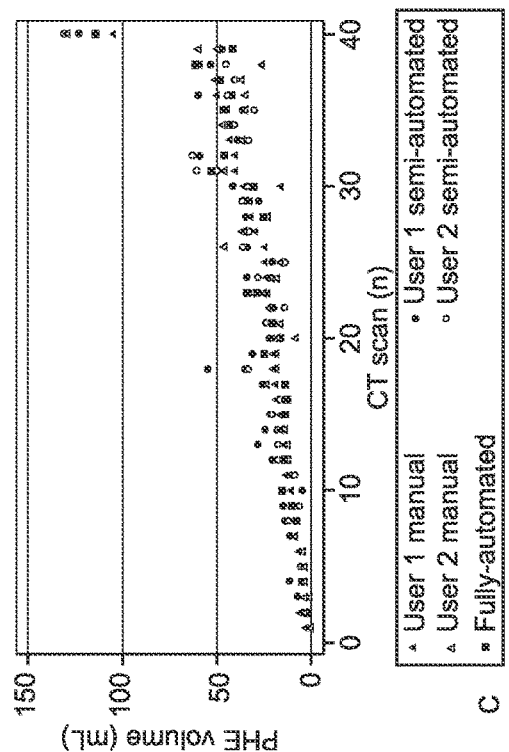
FIG. 8C also shows scatter plot diagrams of PHE volume analysis across segmentation methods according to the various embodiments.
Figure 8D:
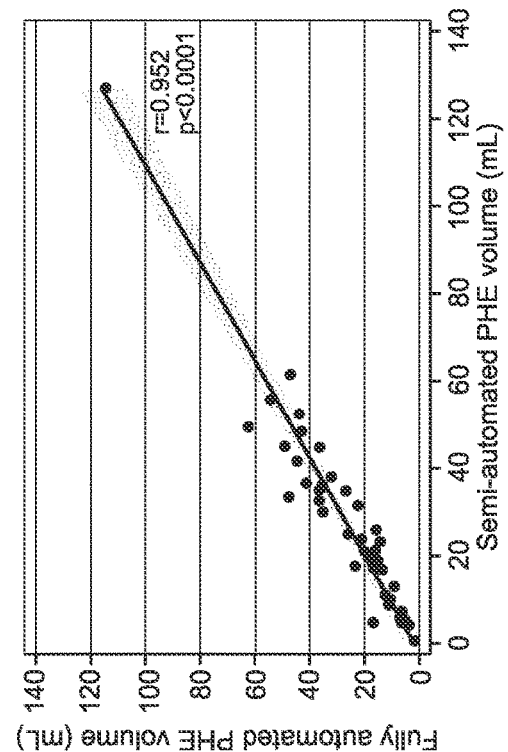
FIG. 8D also shows scatter plot diagrams of PHE volume analysis across segmentation methods according to the various embodiments.

Referring to FIGS. 8A-D, scatter plots are shown for each of the CT image segmentation methods. With reference to FIGS. 1-8D, the performance of various CT image segmentation methods is plotted for the users who performed manual and optionally, semi-automated) segmentation. Scatter plots A-D compare segmented PHE regions across the manual, semi-automated and fully-automated segmentation methods. FIG. 8A shows a comparison of the segmented PHE volumes prepared by each user, applying manual, (optionally semi-automated, and fully automated (CNN model 212) segmentation methods to CT images of the test data set. FIG. 8B shows a comparison of mean segmented PHE volumes among both users resulting from the application of fully automated vs manual segmentation to the CT images of the test data set. FIG. 8C shows a comparison of mean segmented PHE volumes among both users resulting from the application of fully automated vs semi-automated segmentation to the CT images of the test data set. FIG. 8D shows a comparison of mean segmented PHE volumes among both users resulting from the application of semi-automated vs manual segmentation to the CT images of the test data set. Strong between-group correlations may be observed between fully automated versus manual (r=0.964 [0.932-0.981]; P<0.0001; FIG. 3B), fully automated versus semi-automated (r=0.952 [0.910-0.974]; P<0.0001; FIG. 3C), and semi-automated versus manual (r=0.965 [0.935-0.982]; P<0.0001; FIG. 3D) segmentation methods.

Figure 9A:
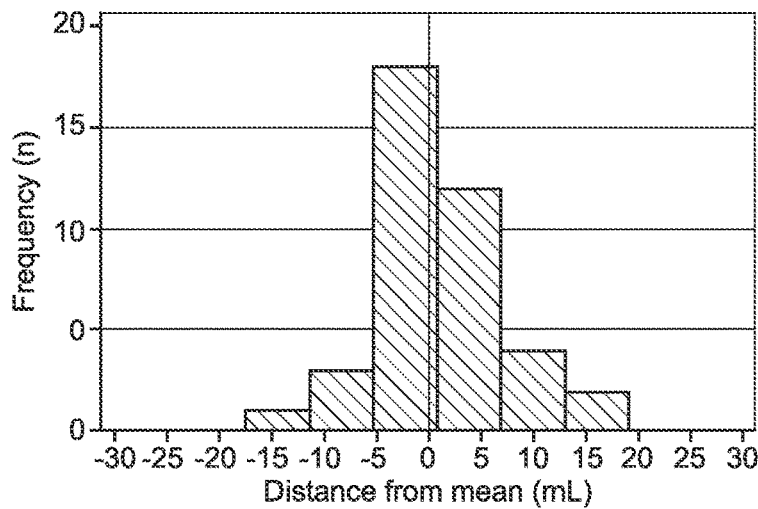
FIG. 9A shows histogram plots of differences in PHE volumes across segmentation methods according to the various embodiments.
Figure 9B:
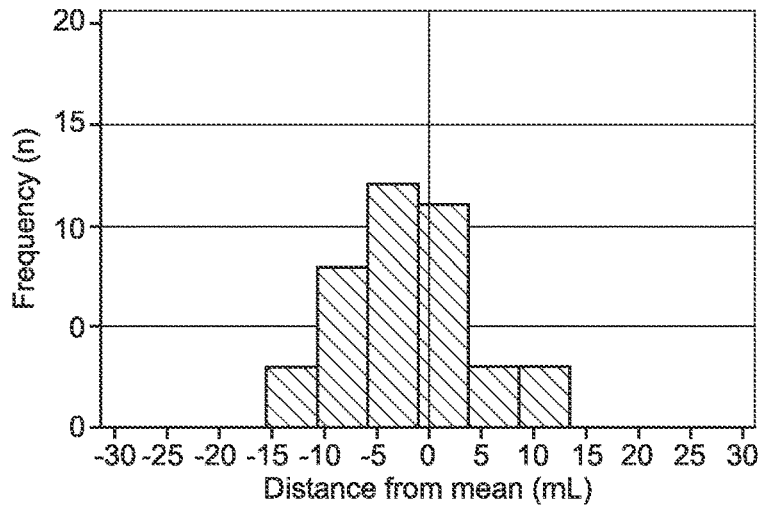
FIG. 9B also shows histogram plots of differences in PHE volumes across segmentation methods according to the various embodiments.
Figure 9C:
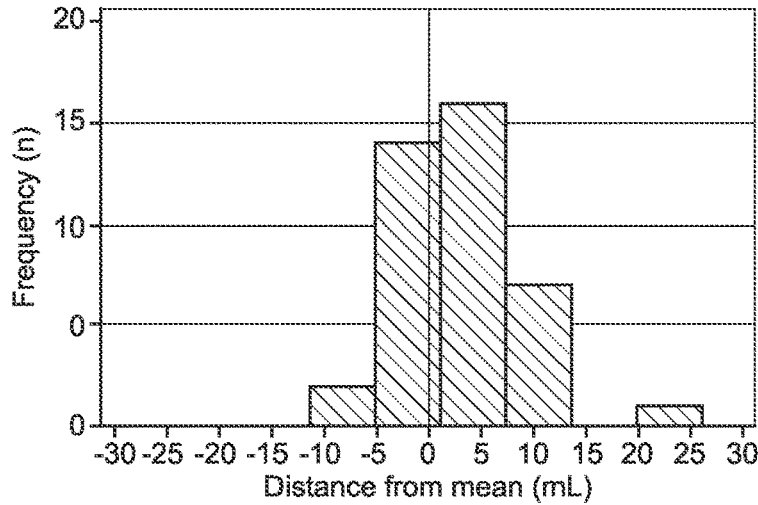
FIG. 9C also shows histogram plots of differences in PHE volumes across segmentation methods according to the various embodiments.

Referring now to FIGS. 9A-C, there are histogram charts showing the differences in segmented PHE volumes across segmentation methods. With reference to FIGS. 1-9C, plotted differences in segmented PHE volumes for each CT image are shown for each applied segmentation method. In FIG. 9A, the differences between the resulting segmented PHE volumes from fully automated versus manual segmentation methods are shown. FIG. 9B shows the differences between the resulting segmented PHE volumes from fully automated versus semi-automated segmentation methods applied to the CT images of the test data set. FIG. 9C shows the differences between the resulting segmented PHE volumes from manual versus semi-automated segmentation methods applied to the CT images of the test data set.

IV. Diagnostic Improvements

In block 310 of FIG. 3, the processor 230 may utilize the CNN model to perform CT image analysis on one or more CT images of a patient. For example, the processor 230 may pass received CT images to the CNN model 212 as the input to obtain an estimate of PHE volumetry presentation and changes. Various embodiments include the use of the trained and tested CNN model 212 to identify and diagnoses changes in PHE volume as distinguished from ICH volumes in patients. The computing device 102 may receive patient CT images from the one or more CT imaging devices 104A-C, throughout the lifecycle of patient care. The computing device 102 may receive these CT images and store them in image data 210 along with a patient identifier. The slices of the CT image may be converted into feature vectors, which are passed as inputs to the CNN model 212.

In block 312 of FIG. 3, the processor 230 may use the output of the CNN model 212 to identify changes in PHE volumetry and diagnose these changes. For example, the processor 230 may execute diagnostic module 218 to compare or otherwise analyze the output of the CNN model 212 executing on the feature vectors of the received patient CT images. The results of the CNN model may be an output that enables diagnosis of PHE volumetry changes, e.g. shape, size, density, etc. This may be the use of diagnostic module 218 to compare CNN model results across CT image slices or 3D CT image stacks for a patient. Alternatively, the diagnostic module 218 may use the direct output of the CNN model as a measurement of difference or change.

In some embodiments, the difference, whether calculated or directly obtained from the CNN model, may be compared to one or more thresholds to determine if the volumetry of the PHE region has grown or subsided significantly. Based on the results of this comparison, the PHE region is diagnosed as either growing or shrinking. That is, if the difference exceeds an upper threshold, then the PHE region may be said to be growing. However, if the difference is below a lower threshold, the PHE region may be said to be shrinking. Differences may be stored along with the image data or tracked in a patient database elsewhere in the network environment 100. If the PHE region is said to be growing, this information may be used to implement various treatments for the patient including surgery, medicines or the like. If the PHE region is said to be shrinking, this may be used to characterize a success in treatment. Diagnoses of PHE region changes may also be used in medical research efforts to study their effects on patient outcomes. For example, if the PHE region is said to be changing, this information may be stored in a patient database elsewhere in the network environment to analyze differences in patient characteristics such as medical history, laboratory studies or genetic markers and/or differences in long term neurological impairment or survival between patients with or without these PHE region changes (i.e. shape, size, density, growth, shrinkage). Diagnoses of PHE region changes may be used in medical research efforts to test the effects of new therapeutics such as medications. The therapy may be termed "effective" if PHE region shrinkage is achieved after its administration.

The above-described embodiments provide solutions to rapid PHE volumetry analysis challenges using a CNN model trained on CT images of patients known to have ICH. By enabling the identification and visualization of PHE volumetry changes, the various embodiments may improve the efficiency and standardization of hematoma change diagnosis. By improving the speed of PHE volumetry changes with no loss of accuracy, the various embodiments improve the speed with which life-saving interventions may be applied to patients. They also reduce the measurement error between different humans performing the same task, thereby improving the precision of these measurements. The disclosed embodiments distinguish the area affected by the ICH from the PHE volume primarily due to the design of the CNN architecture and the training phase where it learns to identify PHE using the training manual segmentations that do not contain ICH information. The windowing differential is a preprocessing step to help to delineate the border between the ICH and the PHE, which helps the CNN model during the training phase.

The above description is intended to be illustrative, and not restrictive. Many other implementations are apparent upon reading and understanding the above description. The scope of the disclosure should be determined with reference to the appended claims, along with the full scope of equivalents to which such claims are entitled.

In the above description, numerous details are set forth. It is apparent, however, that the disclosure may be practiced without these specific details. In some instances, structures and devices are shown in block diagram form, rather than in detail, in order to avoid obscuring the disclosure.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, as apparent from the following discussion, it is appreciated that throughout the description, discussions utilizing terms such as "receiving", "determining", "identifying", "updating", "copying", "publishing", "selecting", "utilizing" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The disclosure also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems appears as set forth in the description below. In addition, the disclosure is not described with reference to any particular programming language. It is appreciated that a variety of programming languages may be used to implement the teachings of the disclosure as described herein. The disclosure may be provided as a computer program product, or software, that may include a machine-readable medium having stored thereon instructions, which may be used to program a computer system (or other electronic devices) to perform a process according to the disclosure. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., carrier waves, infrared signals, digital signals, etc.)), etc.

It is to be understood that the above description is intended to be illustrative, and not restrictive. Many other implementation examples are apparent upon reading and understanding the above description. Although the disclosure describes specific examples, it is recognized that the systems and methods of the disclosure are not limited to the examples described herein, but may be practiced with modifications within the scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

What is claimed is:

1. A computing device for perihematomal edema (PHE) analysis comprising:
   a processor;
   a network communication interface;
   a memory in communication with the processor and having stored thereon, processor-executable instructions for causing the processor to perform operations comprising:
      receiving, from a computerized tomography (CT) imaging device, a three-dimensional CT image of a patient exhibiting PHE in at least a portion of tissue surrounding and external to an intracerebral hematoma (ICH);
      converting the three-dimensional CT image into two-dimensional CT image slices;
      applying Hounsfield Unit (HU) windowing to each two-dimensional CT image slice to differentiate the ICH from the PHE;
      converting each two-dimensional CT image slice into a feature vector;
      passing the feature vectors to a convolutional neural network (CNN) model as input;
      executing the CNN model using the feature vectors of the two-dimensional CT image slices to obtain an estimate of change in PHE volumetry distinct from the ICH using at least one secondary performance parameter including a Hausdorff distance; and
      based on the estimate of change in PHE volumetry, determining a change in a medical status of a PHE volume of the patient according to whether the PHE volume is expanding or shrinking.

2. The computing device of claim 1, wherein determining a change in the medical status of the PHE volume of the patient further comprises:
   comparing the estimate obtained from the CNN model to a threshold; and
   based on the results of the comparison, determining a change in the medical status of the PHE volume of the patient.

3. The computing device of claim 2, wherein the memory has stored therein, instructions for causing the processor to execute operations further comprising:
   determining a treatment plan for the patient based, at least in part, on the change in the medical status of the PHE volume of the patient.

4. The computing device of claim 1, wherein executing the CNN model to obtain an estimate of PHE volumetry is performed for each CT image slice of the CT image; and
   wherein determining a change in the medical status of the PHE volume of the patient further comprises:
      comparing the estimate obtained from the CNN model for each CT image slice; and
      based on the results of the comparison, determining a change in the medical status of the PHE volume of the patient.

5. The computing device of claim 4, wherein the memory has stored therein, instructions for causing the processor to execute operations further comprising:
   determining a treatment plan for the patient based, at least in part, on the change in the medical status of the PHE volume of the patient.

6. The computing device of claim 1, wherein the CNN model is trained on a set of manually segmented CT images including PHE.

7. The computing device of claim 1, wherein the at least one secondary performance parameter includes a mean surface distance, a relative volume difference, or a dice co-efficient.

8. A computing device for perihematomal edema (PHE) analysis comprising:
   a processor;
   a network communication interface;
   a memory in communication with the processor and having stored therein, processor-executable instructions for causing the processor to perform operations comprising:
      receiving, from a computerized tomography (CT) imaging device, a CT image including a plurality of CT image slices of a patient exhibiting PHE in at least a portion of tissue surrounding and external to an intracerebral hematoma (ICH);
      applying Hounsfield Unit (HU) windowing to the CT image slice to differentiate the ICH from the PHE;
      converting the CT image into a feature vector;
      passing the feature vector to a convolutional neural network (CNN) model as input;
      executing the CNN model to obtain an estimate of change in PHE volumetry distinct from the ICH using at least one secondary performance parameter including a Hausdorff distance; and
      based on the estimate of change in PHE volumetry, determining a change in a medical status of a PHE volume of the patient according to whether the PHE volume is expanding or shrinking.

9. The computing device of claim 8, wherein the at least one secondary performance parameter includes a mean surface distance, a relative volume difference, or a dice co-efficient.

10. The computing device of claim 8, wherein executing the CNN model to obtain an estimate of PHE volumetry is performed for each CT image slice of the CT image; and
    wherein determining a change in the medical status of the patient's PHE volume further comprises:
       comparing the estimate obtained from the CNN model for each CT image slice; and
       based on the results of the comparison, determining a change in the medical status of the PHE volume of the patient.

11. The computing device of claim 10, wherein the memory has stored therein, instructions for causing the processor to execute operations further comprising:
    determining a treatment plan for the patient based, at least in part, on the change in the medical status of the PHE volume of the patient.

12. The computing device of claim 8, wherein the CNN model is trained on a set of manually segmented CT images including PHE.

13. A method of perihematomal edema (PHE) analysis comprising
    receiving, via a network communication interface of a computing device, from a computerized tomography (CT) imaging device, a CT image of a patient exhibiting PHE in at least a portion of tissue surrounding and external to an intracerebral hematoma (ICH);
    separating the CT image into CT image slices;
    applying Hounsfield Unit (HU) windowing to each CT image slice to differentiate the ICH from the PHE;
    converting, via a processor of the computing device, each CT image slice into a feature vector;
    passing the feature vectors to a convolutional neural network (CNN) model as input;
    executing the CNN model to obtain an estimate of change in PHE volumetry distinct from the ICH using at least one secondary performance parameter including a Hausdorff distance; and
    based on the estimate of change in PHE volumetry, determining a change in a medical status of a PHE volume of the patient according to whether the PHE volume is expanding or shrinking.

14. The method of claim 13, wherein the CNN model is trained on a set of manually segmented CT images including PHE.

15. The method of claim 13, wherein the at least one secondary performance parameter includes a mean surface distance, a relative volume difference, or a dice co-efficient.

16. The method of claim 13, wherein determining a change in the medical status of the PHE volume of the patient further comprises:
    comparing the estimate obtained from the CNN model to a threshold; and
    based on the results of the comparison, determining a change in the medical status of the PHE volume of the patient.

17. The method of claim 16, further comprising:
    determining a treatment plan for the patient based, at least in part, on the change in the medical status of the PHE volume of the patient.

18. The method of claim 16, wherein executing the CNN model to obtain an estimate of PHE volumetry is performed for each CT image slice of the CT image; and wherein determining a change in the medical status of the PHE volume of the patient further comprises:
    comparing the estimate obtained from the CNN model for each CT image slice; and based on the results of the comparison, determining a change in the medical status of the PHE volume of the patient.

19. The method of claim 18, further comprising:
determining a treatment plan for the patient based, at least in part, on the change in the medical status of the PHE volume of the patient.

\* \* \* \* \*